US011400232B2

(12) United States Patent
Schader et al.

(10) Patent No.: US 11,400,232 B2
(45) Date of Patent: Aug. 2, 2022

(54) DRUG DELIVERY DEVICE

(71) Applicant: SANOFI, Paris (FR)

(72) Inventors: Marc Schader, Frankfurt am Main (DE); William Timmis, Cambridgeshire (GB); James Green, Cambridgeshire (GB)

(73) Assignee: Sanofi, Paris (FR)

( * ) Notice: Subject to any disclaimer, the term of this patent is extended or adjusted under 35 U.S.C. 154(b) by 149 days.

(21) Appl. No.: 16/759,789

(22) PCT Filed: Nov. 1, 2018

(86) PCT No.: PCT/EP2018/079917
§ 371 (c)(1),
(2) Date: Apr. 28, 2020

(87) PCT Pub. No.: WO2019/086563
PCT Pub. Date: May 9, 2019

(65) Prior Publication Data
US 2021/0369966 A1 Dec. 2, 2021

(30) Foreign Application Priority Data

Nov. 3, 2017 (EP) ..................................... 17306522

(51) Int. Cl.
*A61M 5/315* (2006.01)
*A61M 5/31* (2006.01)

(52) U.S. Cl.
CPC ........ *A61M 5/3157* (2013.01); *A61M 5/3146* (2013.01); *A61M 2205/581* (2013.01); *A61M 2205/582* (2013.01)

(58) Field of Classification Search
CPC ...... A61M 2205/582; A61M 2205/581; A61M 5/3157; A61M 5/2033; A61M 5/24; A61M 5/3146; A61M 5/20
See application file for complete search history.

(56) References Cited

U.S. PATENT DOCUMENTS

| 4,629,454 A | 12/1986 | Grier |
| 4,693,711 A | 9/1987 | Bremer et al. |

(Continued)

FOREIGN PATENT DOCUMENTS

| CN | 200987443 | 12/2007 |
| CN | 101107032 | 1/2008 |

(Continued)

OTHER PUBLICATIONS

PCT International Search Report and Written Opinion in Application No. PCT/EP2018/079917, dated Dec. 5, 2018, 10 pages.

(Continued)

*Primary Examiner* — Tiffany Legette
(74) *Attorney, Agent, or Firm* — Fish & Richardson P.C.

(57) ABSTRACT

The present disclosure relates to an audible and/or tactile indicator for use with a drug delivery device including a resilient force member configured to reside in two or more states having two or more different conformations, wherein in a relaxed state, the resilient force member is relaxed in a first conformation, wherein in a biased state, the resilient force member is biased to store energy in a second conformation different to the first conformation, wherein the resilient force member releases stored energy to generate an audible signal when changing from the biased state into the relaxed state due to a transition from the second conformation to the first conformation, wherein the resilient force member is bent by a certain angle about a longitudinal axis forming a longitudinal round fold with two adjacent angled wing-shaped sections.

26 Claims, 9 Drawing Sheets

(56) References Cited

U.S. PATENT DOCUMENTS

| | | |
|---|---|---|
| 4,810,249 A | 3/1989 | Haber et al. |
| 5,114,406 A | 5/1992 | Gabriel et al. |
| 5,116,313 A | 5/1992 | McGregor |
| 5,127,906 A | 7/1992 | Landry et al. |
| 5,271,527 A | 12/1993 | Haber et al. |
| 5,391,157 A | 2/1995 | Harris et al. |
| 7,611,495 B1 | 11/2009 | Gianturco |
| 8,979,807 B2 | 3/2015 | Grunhut et al. |
| 9,168,339 B2 | 10/2015 | Cowe |
| 9,199,038 B2 | 12/2015 | Daniel |
| 9,216,251 B2 | 12/2015 | Daniel |
| 9,744,306 B2 | 8/2017 | Cowe |
| 9,764,096 B2 | 9/2017 | Maritan |
| 2004/0210199 A1 | 10/2004 | Atterbury et al. |
| 2007/0088248 A1 | 4/2007 | Glenn et al. |
| 2008/0021373 A1 | 1/2008 | Rosati |
| 2010/0198182 A1 | 8/2010 | Lanigan et al. |
| 2011/0026721 A1 | 2/2011 | Parker |
| 2011/0105952 A1 | 5/2011 | Bernstein et al. |
| 2013/0023749 A1 | 1/2013 | Afanasewicz et al. |
| 2013/0090605 A1 | 4/2013 | O'Connor et al. |
| 2013/0906605 | 4/2013 | O'Connor et al. |
| 2013/0345642 A1 | 12/2013 | Cowe |
| 2014/0114250 A1 | 4/2014 | Salvo et al. |
| 2014/0243751 A1 | 8/2014 | Brereton et al. |
| 2014/0276568 A1 | 9/2014 | Worden et al. |
| 2015/0265772 A1 | 9/2015 | Maritan |
| 2016/0008541 A1 | 1/2016 | Hirschel et al. |
| 2016/0008542 A1 | 1/2016 | Hirschel et al. |
| 2016/0015899 A1 | 1/2016 | Plumptre et al. |
| 2016/0144133 A1 | 5/2016 | Kemp |
| 2018/0154078 A1* | 6/2018 | Mosebach ............ A61M 5/2033 |

FOREIGN PATENT DOCUMENTS

| | | |
|---|---|---|
| CN | 201111673 | 9/2008 |
| CN | 201243374 | 5/2009 |
| CN | 102209564 | 10/2011 |
| CN | 102842236 | 12/2012 |
| CN | 202887394 | 4/2013 |
| CN | 103177716 | 6/2013 |
| CN | 103235538 | 8/2013 |
| CN | 104080499 | 10/2014 |
| CN | 104519929 | 4/2015 |
| CN | 105188809 | 12/2015 |
| CN | 105327432 | 2/2016 |
| CN | 105451792 | 3/2016 |
| CN | 106573114 | 4/2017 |
| DE | 7833454 | 5/1979 |
| DE | 3935672 | 11/1990 |
| EP | 2727617 | 5/2014 |
| EP | 2868338 | 5/2015 |
| EP | 3302632 | 9/2020 |
| JP | H06-190041 | 7/1994 |
| JP | H07-509636 | 10/1995 |
| JP | 2005-508205 | 3/2005 |
| JP | 2011-519712 | 7/2011 |
| JP | 2012-504006 | 2/2012 |
| JP | 2013-526894 | 6/2013 |
| JP | 2013-526904 | 6/2013 |
| JP | 2013-146600 | 8/2013 |
| JP | 2013-534164 | 9/2013 |
| JP | H5-508098 | 5/2014 |
| JP | 2014-526298 | 10/2014 |
| JP | 2015-536184 | 12/2015 |
| JP | 2016-512766 | 5/2016 |
| JP | 2016-513507 | 5/2016 |
| RU | 2140794 | 11/1999 |
| RU | 2012137269 | 3/2014 |
| WO | WO 92/17223 | 10/1992 |
| WO | WO 94/03222 | 2/1994 |
| WO | WO 02/092153 | 11/2002 |
| WO | WO 2005/046773 | 5/2005 |
| WO | WO 2006/079481 | 8/2006 |
| WO | WO 2009/140251 | 11/2009 |
| WO | WO 2010/035057 | 4/2010 |
| WO | WO 2011/079278 | 6/2011 |
| WO | WO 2011/123024 | 10/2011 |
| WO | WO 2012/022810 | 2/2012 |
| WO | WO 2012/045350 | 4/2012 |
| WO | WO 2013/034984 | 3/2013 |
| WO | WO 2013/057033 | 4/2013 |
| WO | WO 2013/057034 | 4/2013 |
| WO | WO 2014/005808 | 1/2014 |
| WO | WO 2014/066461 | 5/2014 |
| WO | WO 2014/139914 | 9/2014 |
| WO | WO 2014/139922 | 9/2014 |
| WO | WO 2014/146209 | 9/2014 |
| WO | WO 2014/164943 | 10/2014 |
| WO | WO 2015/004050 | 1/2015 |
| WO | WO 2015/019071 | 2/2015 |
| WO | WO 2015/062915 | 5/2015 |
| WO | WO 2016/001304 | 1/2016 |
| WO | WO 2016/193343 | 12/2016 |
| WO | WO 2016/193344 | 12/2016 |

OTHER PUBLICATIONS

PCT International Preliminary Report on Patentability in Application No. PCT/EP2018/079917, dated May 5, 2020, 8 pages.

Engineers Edge, "Transducers USA Announced Improved TRIP60 Series of Audio Alerts", Engineering and Technology News, Aug. 2007, 3 pages.

PCT International Preliminary Report on Patentability in International Appln. No. PCT/EP2018/079915, dated May 5, 2020, 8 pages.

Karpova, "The basics of surdopedagogy", Ekaterinburg, pp. 20-21, 2008.

PCT International Preliminary Report on Patentability in International Appln. No. PCT/EP2016/062449, dated Dec. 5, 2017, 6 pages.

PCT International Preliminary Report on Patentability in International Appln. No. PCT/EP2016/062450, dated Dec. 5, 2017, 7 pages.

PCT International Preliminary Report on Patentability in International Appln. No. PCT/EP2016/062452, dated Dec. 5, 2017, 7 pages.

PCT International Preliminary Report on Patentability in International Appln. No. PCT/EP2016/062454, dated Dec. 5, 2017, 7 pages.

PCT International Search Report and Written Opinion in International Appln. No. PCT/EP2016/062449, dated Aug. 17, 2016, 8 pages.

PCT International Search Report and Written Opinion in International Appln. No. PCT/EP2016/062450, dated Aug. 5, 2016, 9 pages.

PCT International Search Report and Written Opinion in International Appln. No. PCT/EP2016/062452, dated Sep. 15, 2016, 11 pages.

PCT International Search Report and Written Opinion in International Appln. No. PCT/EP2016/062454, dated Aug. 5, 2016, 9 pages.

PCT International Search Report and Written Opinion in International Appln. No. PCT/EP2018/079915, dated Dec. 5, 2018, 13 pages.

National Standards of People's Republic of China, "Audible and/or Visual Fire Alarm Signaling Appliances", General Administration of Quality Supervision, Inspection and Quarantine of the People's Republic of China, Jul. 2011, 39 pages (with machine translation).

National Standards of People's Republic of China, "Fire Detection and Alarm Systems—Smoke Alarms", General Administration of Quality Supervision, Inspection and Quarantine of the People's Republic of China, Jul. 2006, 45 pages (with machine translation).

National Standards of People's Republic of China, "Vehicle Electronic Sirens", General Administration of Quality Supervision, Inspection and Quarantine of the People's Republic of China, Dec. 2014, 31 pages (with machine translation).

* cited by examiner

DRUG DELIVERY DEVICE

CROSS-REFERENCE TO RELATED APPLICATIONS

The present application is the national stage entry of International Patent Application No. PCT/EP2018/079917, filed on Nov. 1, 2018, and claims priority to Application No. EP 17306522.8, filed on Nov. 3, 2017, the disclosures of which are incorporated herein by reference.

TECHNICAL FIELD

The disclosure generally relates to a drug delivery device having an audible and/or tactile indicator.

BACKGROUND

Administering an injection or drug is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Furthermore, the force required to push the button/plunger may be too high (e.g., if the user is elderly or a child). And, aligning the injection device, administering the injection, and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is necessary to administer the full dose in order to achieve full effectiveness of the medicament within the patient.

SUMMARY

The present disclosure provides an improved audible and/or tactile indicator for use with a drug delivery device and an improved drug delivery device comprising such an audible and/or tactile indicator.

According to the present disclosure, an audible and/or tactile indicator for use with a drug delivery device comprises a resilient force member that is configured to reside in two or more states having two or more different conformations, wherein in a relaxed state, the resilient force member is relaxed in a first conformation, wherein in a biased state, the resilient force member is biased to store energy in a second conformation different to the first conformation, and wherein the resilient force member releases stored energy to generate an audible signal when changing from the biased state into the relaxed state due to a transition from the second conformation to the first conformation, wherein the resilient force member is bent by a certain angle about a longitudinal axis forming a longitudinal round fold with two adjacent angled wing-shaped sections.

The longitudinal round fold reduces stress impact and risk of permanent deformation of the resilient force member during priming of the drug delivery device.

In an exemplary embodiment, a notch is formed into the longitudinal round fold, e.g. extending transversely to the longitudinal round fold. The notch is provided to support consistency of priming during assembly of the audible and/or tactile indicator. In the context of the present disclosure, priming means to move the resilient force member into the biased state.

In an exemplary embodiment, on at least one of the wing-shaped sections a supporting tab is provided outwardly protruding from a long side of the wing-shaped section. The supporting tab is provided to reduce sensitivity to manufacturing variations and to increase drop resistance of the resilient force member. Thus, the drug delivery device is improved in order to achieve a reliable indication of the end of medicament delivery and a full effectiveness of the medicament within the patient.

In an exemplary embodiment, the longitudinal round fold has a bend radius between 1.5 mm and 2 mm. This allows for pre-priming during manufacture of the resilient force member.

According to a further exemplary embodiment, the supporting tab has a free end which is outwardly bent. This increases a reliability of the audible and/or tactile indicator as well as stability under drop.

In accordance with an aspect of the present disclosure, the notch is centrically arranged in the longitudinal round fold with respect to the longitudinal axis. This supports an assembly of the resilient force member in the drug delivery device, which requires bending the resilient force member in the centre about an axis running perpendicular to the longitudinal round fold.

Moreover, the supporting tab may be arranged on a region of the wing-shaped member extending between the notch and one of two end faces of the resilient force member with respect to the longitudinal axis. This increases reliability of function of the audible and/or tactile indication. The drop resistance will be increased as well.

In an exemplary embodiment, the resilient force member is configured as a leaf spring having a longitudinal axis. The leaf spring may comprise a resilient material, e. g. spring steel or spring plastic. Leaf springs are well known and easy to manufacture. The leaf spring may have a rectangular shape, a square shape or an oval shape.

Moreover, the resilient force member, e. g. the leaf spring, may be bent about the longitudinal bend such that the two-wing-shaped sections are at an angle of between 130 degrees and 160 degrees relative to each other. For example, the angle can be between 130 degrees and 140 degrees or between 140 degrees and 155 degrees or between 132 degrees and 142 degrees or between 134 degrees and 140 degrees or between 136 degrees and 138 degrees. In an exemplary embodiment, the angle is approximately or exactly 136 degrees or 137 degrees or 138 degrees or 148 degrees or 152 degrees. The angle provides best balance between noise and reliability.

According to another aspect of the present disclosure, the resilient force member, e. g. the leaf spring, is configured as a bistable spring element. A bistable spring element has two stable states or conformations in which it can rest without support from an external component. In order to move the bistable spring element from one stable state or conformation to the other, energy has to be used to move the bistable spring element into an intermediate state. This energy is then released as the bistable spring moves out of the intermediate state into one of the stable states.

It is understood that a bistable leaf spring can store energy in the form of tension on one or more outer edges of one or more wing-shaped sections. It is also understood that the bistable leaf spring can also store energy in the form of compression in a central region of one or more wing-shaped sections.

In an alternative embodiment, the resilient force member is configured as a monostable spring element. As opposed to a bistable spring element, a monostable spring element may have only one stable state. If resiliently deformed from out of this stable state and subsequently released, the monostable spring element will return to this stable state. In order to keep a monostable spring element in an instable state, an additional component supporting the monostable spring element in the instable state is required.

It is understood that a monostable leaf spring can store energy in the form of tension on one or more outer edges of one or more wing-shaped sections. It is also understood that the monostable leaf spring can also store energy in the form of compression in a central region of one or more wing-shaped sections.

In an exemplary embodiment, the resilient force member is supported in the biased state in order to prevent transition into the relaxed state. This mechanically stabilizes the biased state of the resilient force member.

According to another aspect of the present disclosure, a drug delivery device comprises an audible and/or tactile indicator.

Moreover, the audible and/or tactile indicator may be activated by a movement of a plunger. In particular, the audible and/or tactile indicator is activated by the movement of the plunger towards a proximal position at the end of a medicament delivery process. The plunger is used to displace a drug from a medicament container. For example, the resilient force member transitions from the biased state into the relaxed state when the plunger moves towards or reaches a proximal position at the end of a medicament delivery process.

According to a further exemplary embodiment, the resilient force member transitions from the biased state into the relaxed state when a proximal plunger section abuts a distal end face of the resilient force member.

In an exemplary embodiment, the drug delivery device may comprise a medicament container containing a medicament.

Furthermore, the resilient force member may be supported when the drug delivery device is in an initial state and the resilient force member may be unsupported when the drug delivery device is in a primed state. Alternatively, the resilient force member may be supported when the drug delivery device is in an initial state and in a primed state, wherein a distal end face of the resilient force member is supported by a supporting protrusion arranged on a proximal section of a housing. Alternatively, the resilient force member may be unsupported in the biased state.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all Figures.

DETAILED DESCRIPTION

Figure 1A:
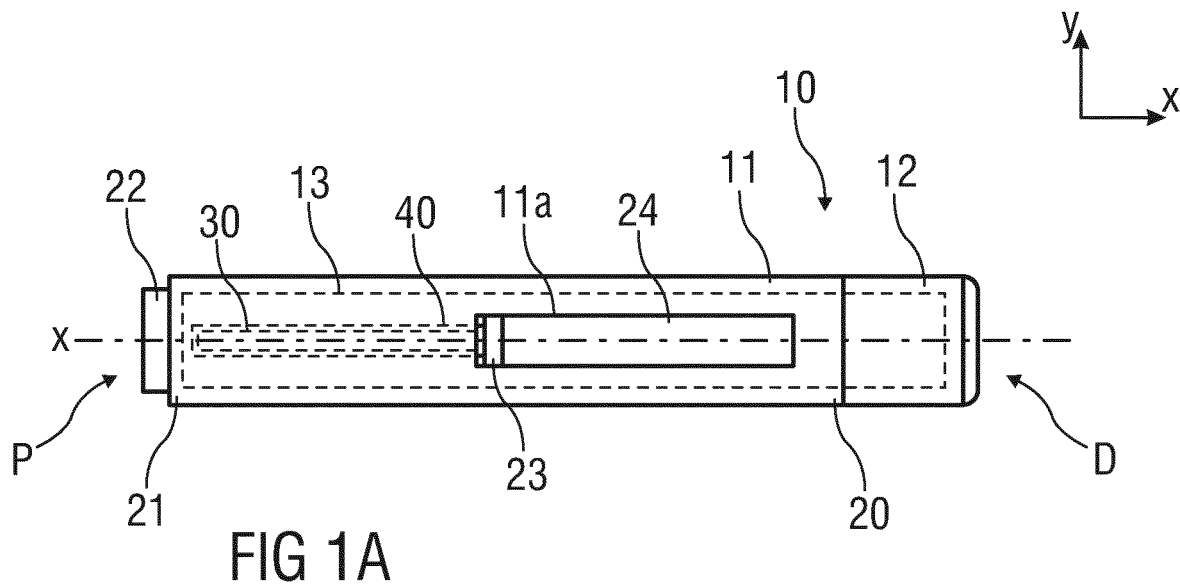
FIG. 1A to 1B are schematic views of drug delivery devices.
Figure 1B:
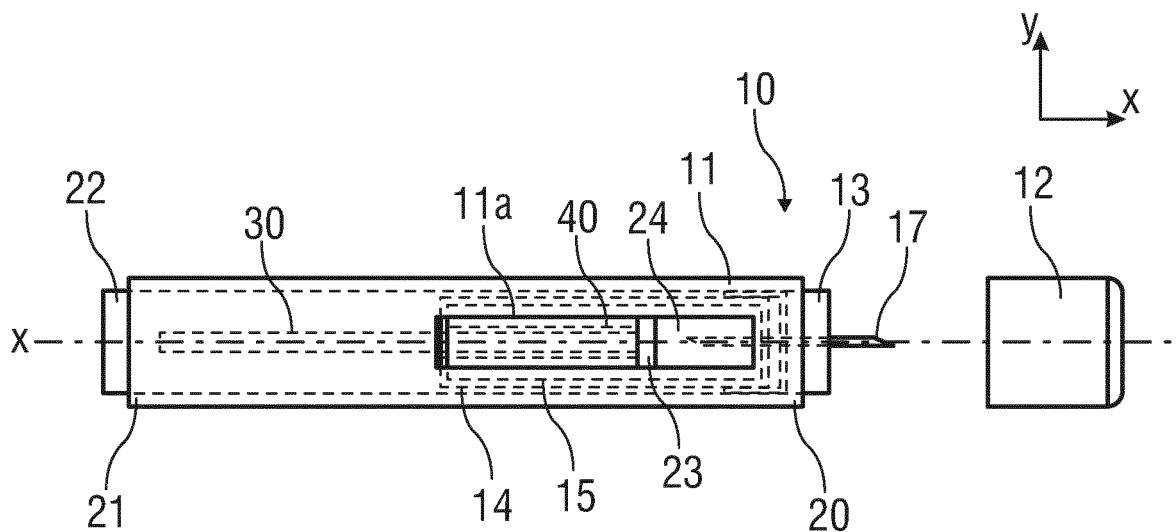

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe 24 within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

Figure 2A:
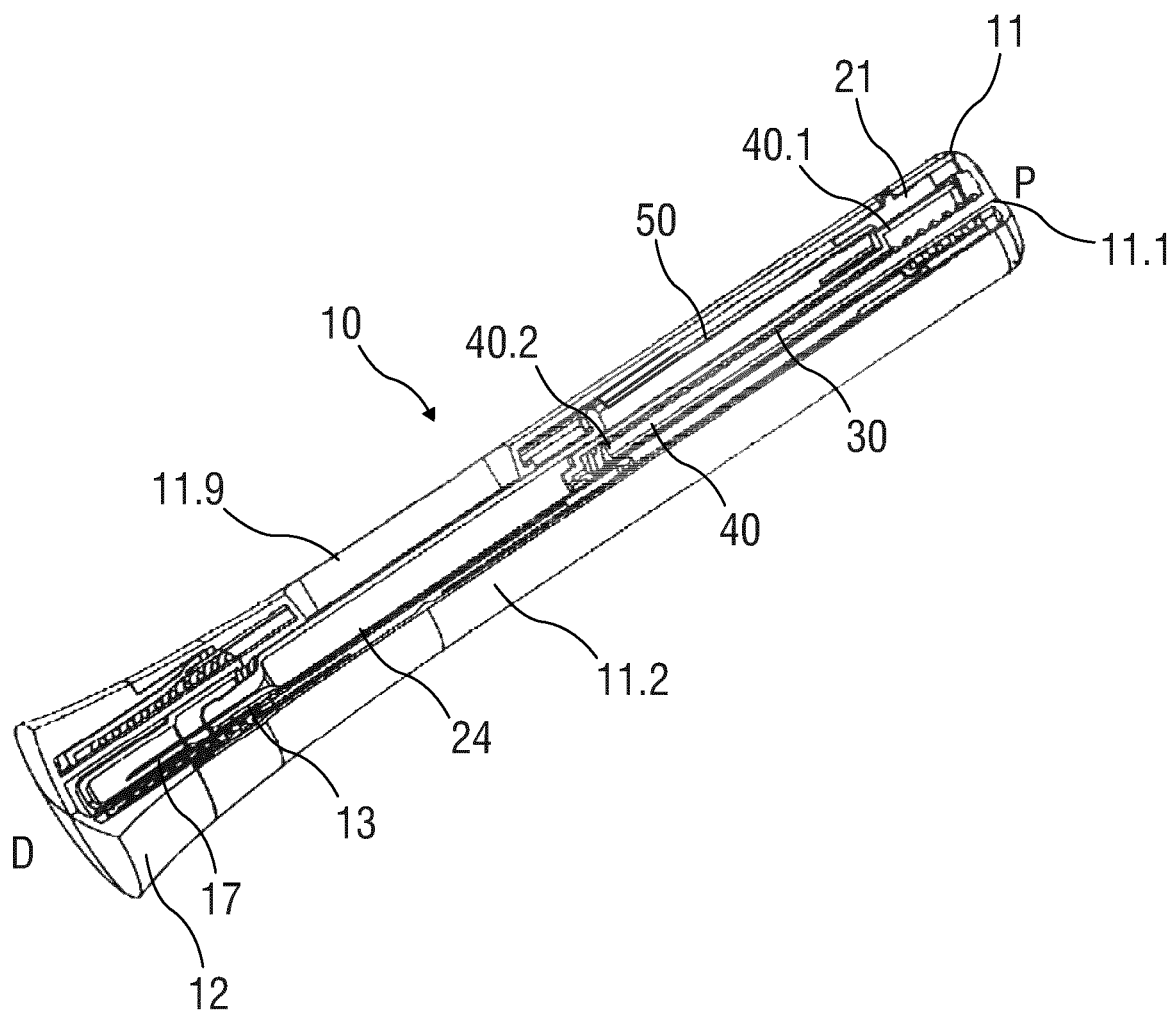
FIG. 2A to 2C are schematic perspective/exploded partial sections of a drug delivery device comprising an audible and/or tactile indicator.

FIG. 2A is a perspective partial section of an exemplary embodiment of a drug delivery device 10 comprising an audible and/or tactile indicator 50. The drug delivery device 10 further comprises the components as described before.

The housing 11 has two parts, a rear case 11.1 and a front case 11.2 which are coupled to each other in the assembled state.

The plunger 40 may comprise a proximal plunger section 40.1 and a distal plunger section 40.2 (see FIGS. 2A, 9 and 10) that are configured with different diameters, wherein the diameter of the proximal plunger section 40.1 is larger than the diameter of the distal plunger section 40.2.

The drug delivery device 10 further comprises the audible and/or tactile indicator 50 that is arranged in the proximal region 21 of the device 10 and that is adapted for producing an audible feedback for a user or patient indicating completion of drug delivery. In other words: The audible and/or tactile indicator 50 is provided to indicate to a user or a patient that the full dose of drug was spent.

Figure 2B:
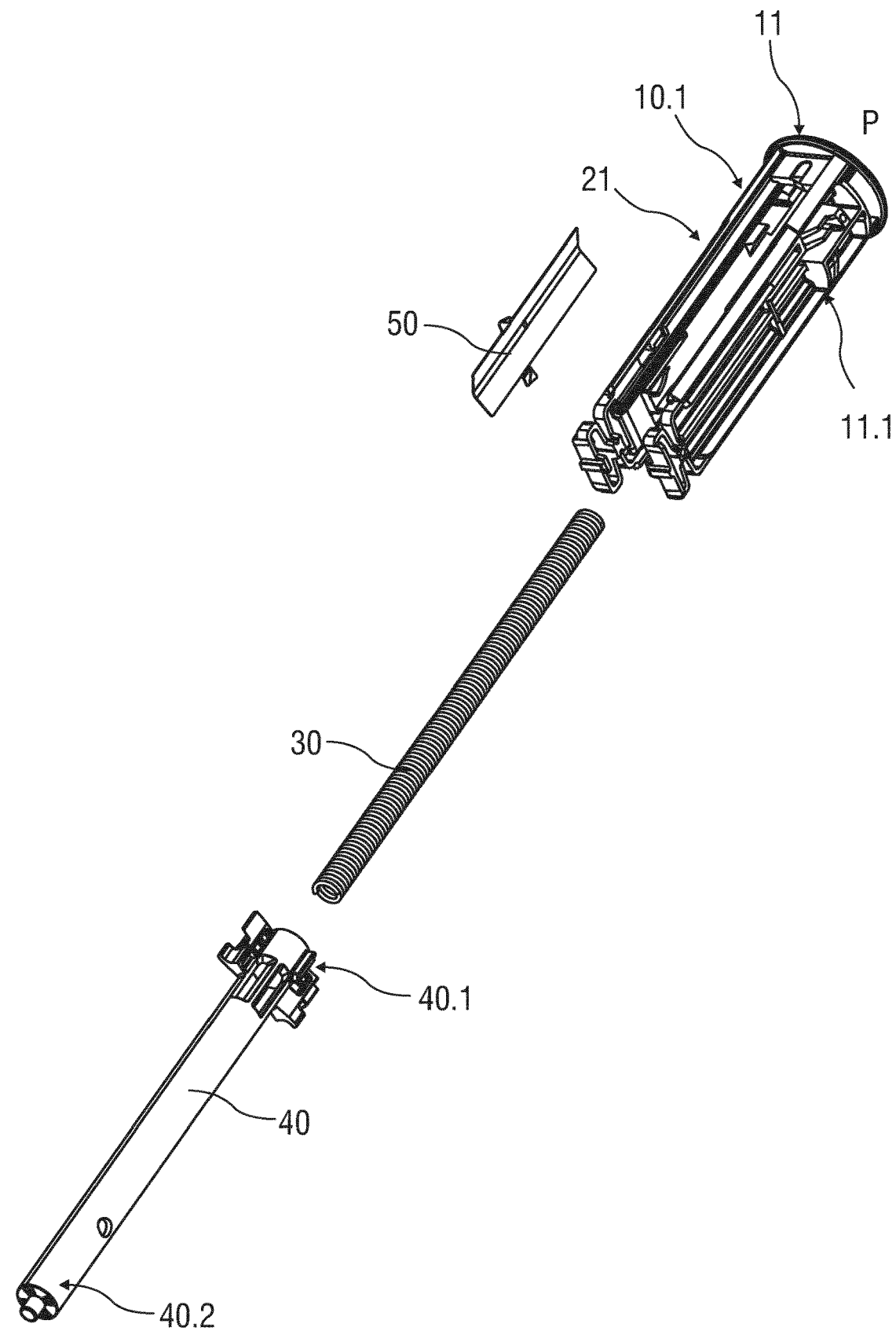

FIG. 2B is an exploded view of the respective components, e.g. the rear case 11.1, the plunger 40 with its proximal plunger section 40.1 and its distal plunger section 40.2, the drive spring 30 and the indicator 50. The rear case 11.1 has inner and outer surfaces forming cavities to contain the indicator 50 and the plunger 40 and, thus, forms a drive sub-assembly 10.1 of the device 10. The plunger 40 has an inner cavity adapted to contain the drive spring 30.

Due to the close arrangement of the indicator 50 to the outer housing 11, in particular the front case 11.1, a transition of the indicator 50 from a biased state S2 into a relaxed state S1 (shown in FIGS. 9 and 10) generates a tactile feedback in a region of the housing 11 which is typically held by a user, in particular at the proximal region 21 of the device 10, in particular of the front case 11.1.

Figure 2C:
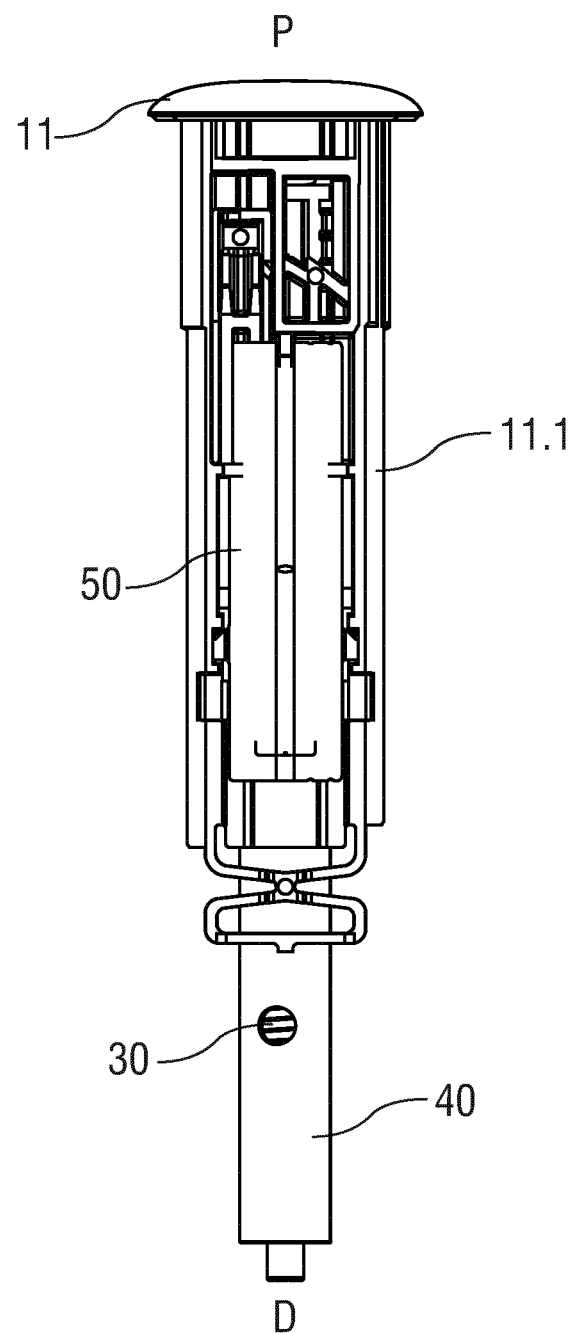

FIG. 2A shows the device 10 in an assembled state. FIG. 2C shows the component of the drive sub assembly 10.1 in an pre-assembled state.

Figure 3A:
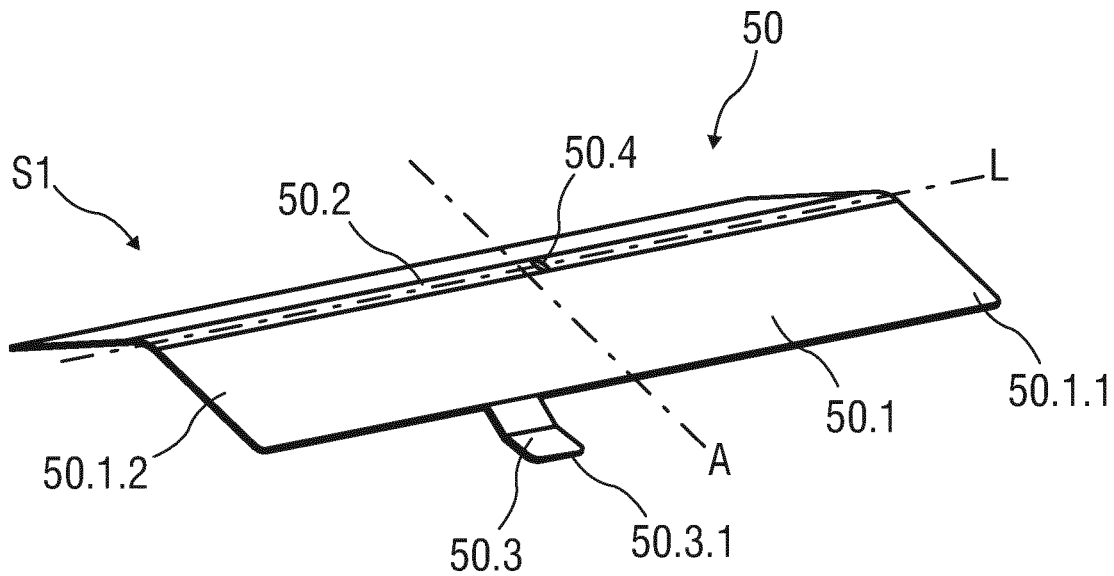
FIG. 3A to 3B are schematic views of audible and/or tactile indicators in different exemplary embodiments.
Figure 3B:
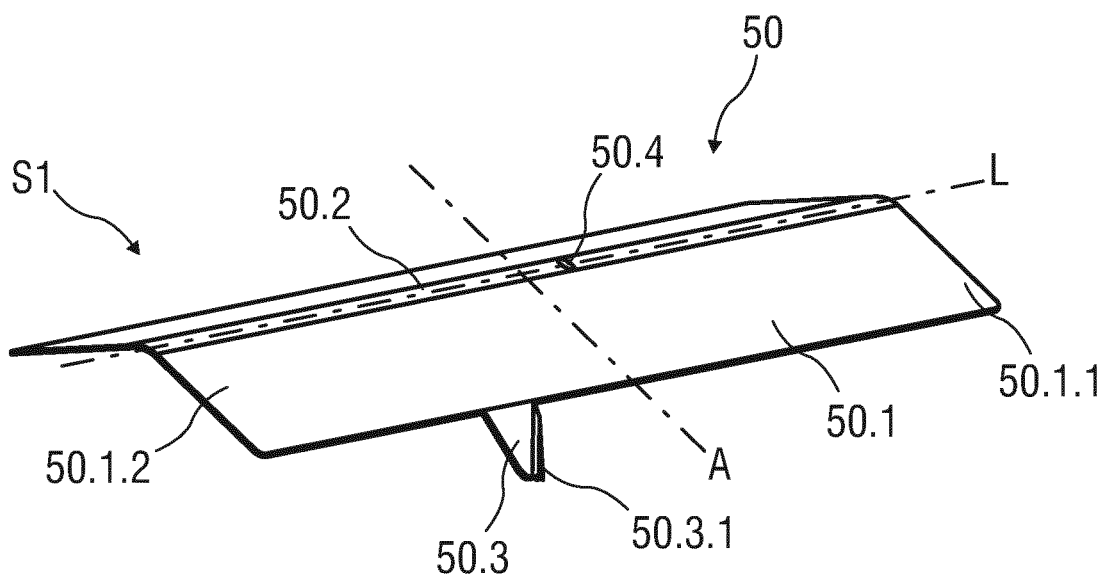

FIGS. 3A and 3B are schematic views of audible and/or tactile indicators 50 in different exemplary embodiments.

Both, FIGS. 3A and 3B show an audible and/or tactile indicator 50 that comprises a resilient force member 50.1 having a substantially rectangular shape and comprising a longitudinal axis L running in parallel to the longest side of the outer circumference of the resilient force member 50.1. In other embodiments, the resilient force member 50.1 may have a triangular shape or any other geometrical shape suitable to couple the audible and/or tactile indicator 50 to the drug delivery device 10.

The resilient force member 50.1 may be designed as a monostable leaf spring comprising a resilient material, e. g., spring steel or spring plastic. Thus, the resilient force member 50.1 is capable of residing in two states. That is, the resilient force member 50.1 may assume two different conformations, one of them stable with limited or no application of an external force and the other one unstable. For example, these two states can include a first or relaxed state S1 (or pre-assembly state, or triggered state), in which the resilient force member 50.1 has a first conformation. In a second or biased state S2 (or primed state, see FIGS. 7 to 9), the resilient force member 50.1 can have a second conformation. In the present FIGS. 3A and 3B, the resilient force member 50.1 is in the relaxed state S1 which can correspond to the pre-assembly state as well as to a state at the end of drug delivery.

The resilient force member 50.1 is bent by a certain angle about the longitudinal axis L forming a longitudinal round fold 50.2 with two adjacent angled wing-shaped sections angled to each other with an angle less than 180 degrees. The longitudinal round fold 50.2 may have a bend radius between 1.5 mm and 2 mm, in particular 1.6 mm +/−0.1 mm. In other embodiments, the bend radius may be outside these ranges. This bend radius reduces a stress impact during priming and the risk of permanent deformation.

The angle between the two adjacent angled wing-shaped sections can be between 130 degrees and 140 degrees or between 140 degrees and 155 degrees or between 132 degrees and 142 degrees or between 134 degrees and 140 degrees or between 136 degrees and 138 degrees. In an exemplary embodiment, the angle is approximately or exactly 136 degrees or 137 degrees or 138 degrees or 148 degrees or 152 degrees. In the present Figure, the wing-shaped sections are angled downwards. The longitudinal round fold 50.2 is located in the centre of the resilient force member 50.1 running in parallel to the longitudinal axis L.

Furthermore, the resilient force member 50.1 comprises one or more supporting tabs 50.3 projecting outwardly from a long side of at least one of the wing-shaped sections. In particular, the resilient force member 50.1 includes a pair of supporting tabs 50.3, wherein each wing-shaped section comprises one supporting tab 50.3. The supporting tabs 50.3 may be respectively arranged between a notch 50.4 and a proximal end face 50.1.2 of the resilient force member 50.1 with respect to the longitudinal axis L in order to increase a reliability of function of the audible and/or tactile indication as well as stability under drop. Furthermore, the supporting tabs 50.3 may be arranged opposite to each other with respect to a cross axis A running perpendicular to the longitudinal axis L.

In order to facilitate assembly of the audible and/or tactile indicator 50 into the drug delivery device 10, the supporting tabs 50.3 respectively have a free end 50.3.1 which is outwardly bent. FIG. 3A illustrates a first embodiment, wherein the supporting tabs 50.3 have a rectangular shape. Respectively, the free end 50.3.1 of the supporting tabs 50.3 is entirely bent upwards in an angle about an axis running perpendicular to the longitudinal axis L and to the cross axis A.

FIG. 3B illustrates a second embodiment, wherein the supporting tabs 50.3 have a rectangular shape as well. Respectively, one edge of the free end 50.3.1 of the supporting tabs 50.3 is bent downwardly and thus perpendicular to the longitudinal axis L and to the cross axis A.

The resilient force member 50.1 further comprises the notch 50.4 that is formed into the longitudinal round fold 50.2 and that extends transversely with respect to the longitudinal round fold 50.2. The notch 50.4 may be centrically arranged in the longitudinal round fold 50.2 with respect to the longitudinal axis L. The notch 50.4 supports priming of the resilient force member 50.1 as illustrated for example in FIG. 7. The notch 50.4 may be configured as an opening or alternatively as a blind hole.

Figure 4:
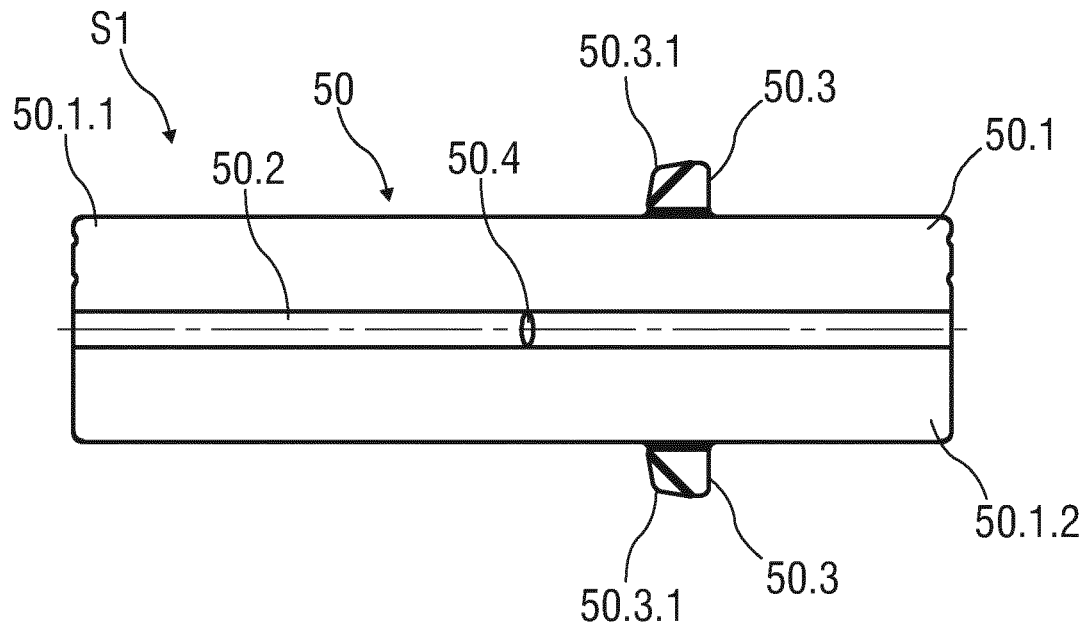
FIG. 4 is a top view of an exemplary embodiment of an audible and/or tactile indicator.
Figure 5:
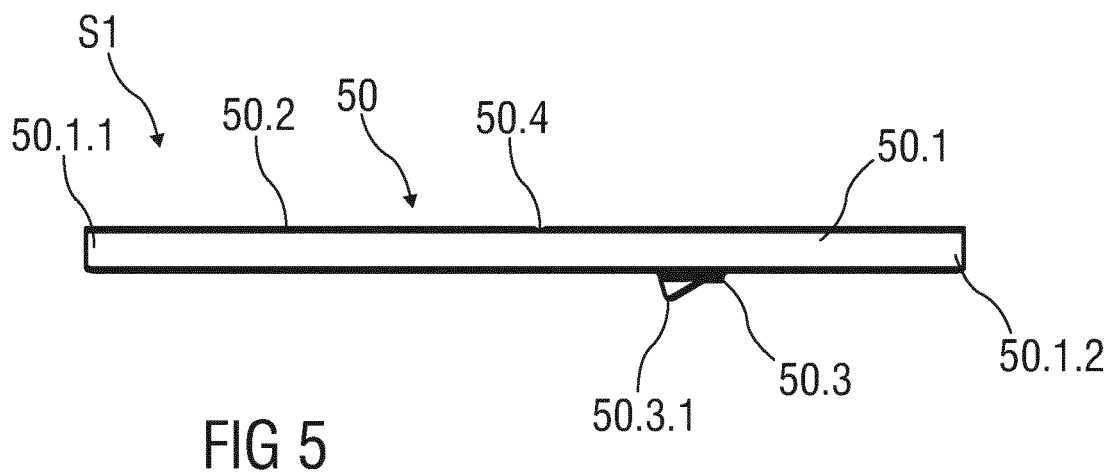
FIG. 5 is a side view of the audible and/or tactile indicator according to FIG. 4.
Figure 6:
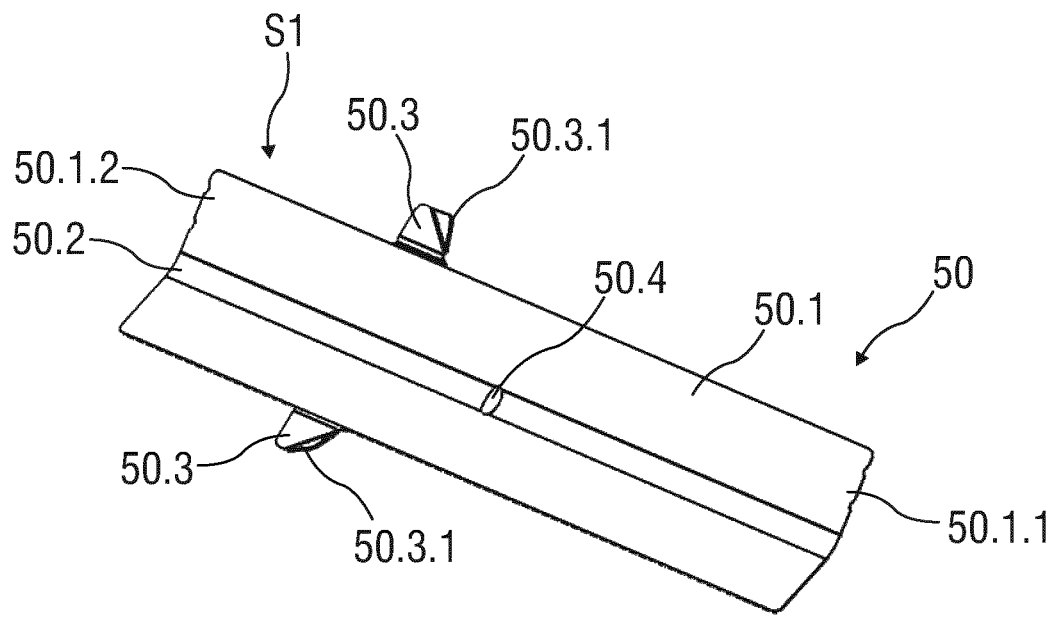
FIG. 6 is a perspective view of the audible and/or tactile indicator according to FIG. 4.
Figure 7:
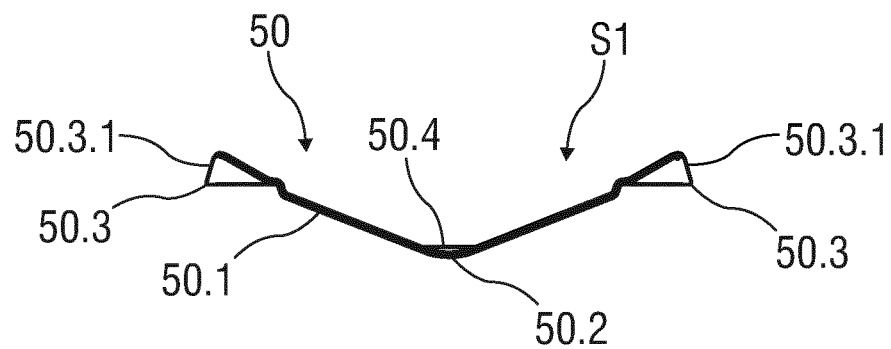
FIG. 7 is a cross section of the audible and/or tactile indicator according to FIG. 4.

The FIGS. 4 to 7 are different views of the drug delivery device 10 according to the second embodiment of FIG. 3B. In particular, FIG. 4 is a top view of the drug delivery device 10. FIG. 5 is a side view of the drug delivery device 10 and FIG. 6 is a perspective view of the drug delivery device 10 having wing-shaped sections angled upwards. FIG. 7 is a cross section of the drug delivery device 10.

For assembling the audible and/or tactile indicator 50 into the drug delivery device 10, the resilient force member 50.1 is bent in the centre about the cross axis A with an angle less than 90 degrees. This bending is achieved by applying a predetermined force onto or near a centre point of the resilient force member 50.1 when engaging the tabs 50.3 within corresponding openings in a proximal region 21 of the housing 11. Due to the bending, the audible and/or tactile indicator 50 transitions the second biased state S2. This transition from the relaxed state S1 into the biased state S2 will be understood as priming of the audible and/or tactile indicator 50.

Figure 8:
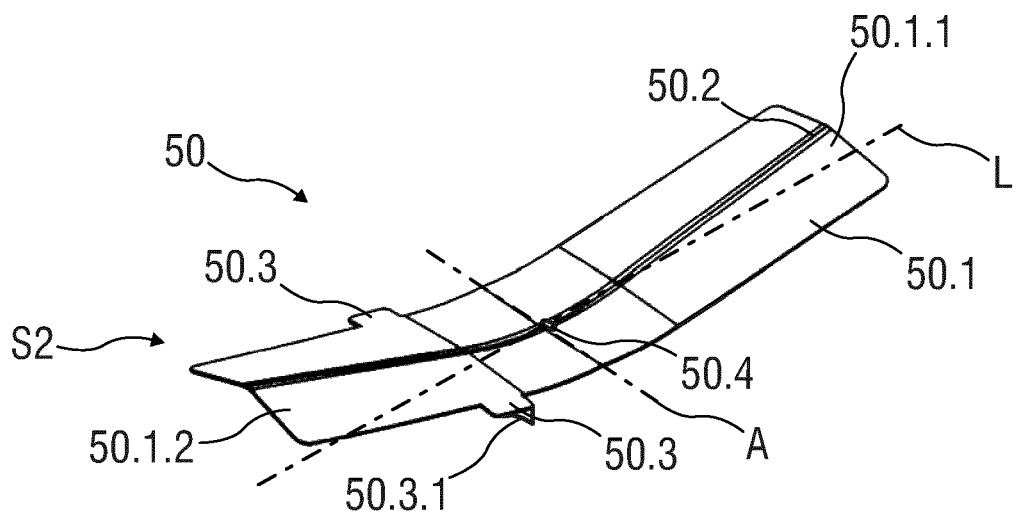
FIG. 8 is a perspective view of the audible and/or tactile indicator according to FIG. 4 in a primed state.

FIG. 8 is a perspective view of the audible and/or tactile indicator 50 according to the second embodiment in the biased state S2.

In the biased state S2, two end faces 50.1.1, 50.1.2 of the resilient force member 50.1 are angled upwards from the centre point. The biased state S2 corresponds with the primed state, wherein the resilient force member 50.1 stores a certain amount of energy. Due to the notch 50.4, priming of the audible and/or tactile indicator 50 is easier and more consistent. After removing the applied force, the resilient force member 50.1 is held in the biased state S2.

The audible and/or tactile indicator 50 is coupled to the housing 11 as illustrated in FIG. 2. In detail, the resilient force member 50.1 is held in the proximal section 21 of the housing 11 such that the longitudinal axis L is in parallel with the longitudinal axis X of the drug delivery device 10. The cross axis A may be in parallel with a cross axis Y of the drug delivery device 10.

The audible and/or tactile indicator 50 is coupled to the drug delivery device 10 by a snap connection, wherein the supporting tabs 50.3 are engaged within a number of corresponding openings (not shown) in the proximal region 21 of the housing 11. Alternatively, the resilient force member 50.1 may be held in the proximal section 21 of the housing 11 by a frictional connection, such as a screw or rivet connection or interference fit.

Figure 9:
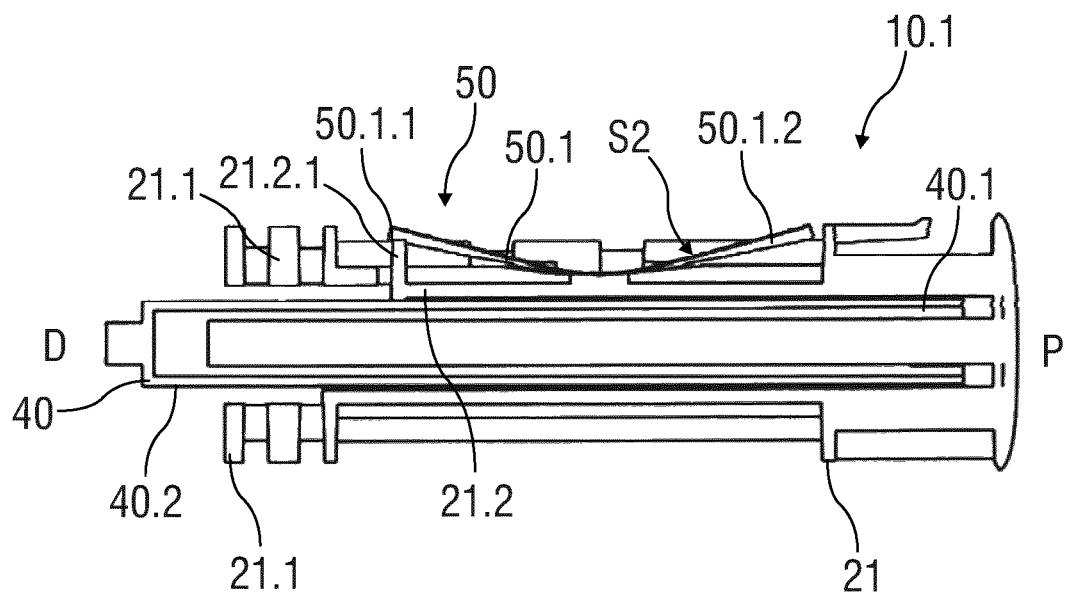
FIG. 9 is a longitudinal section of a drive sub assembly of a drug delivery device comprising a rear case, a plunger and the audible and/or tactile indicator according to FIG. 8 in the primed state
Figure 10:
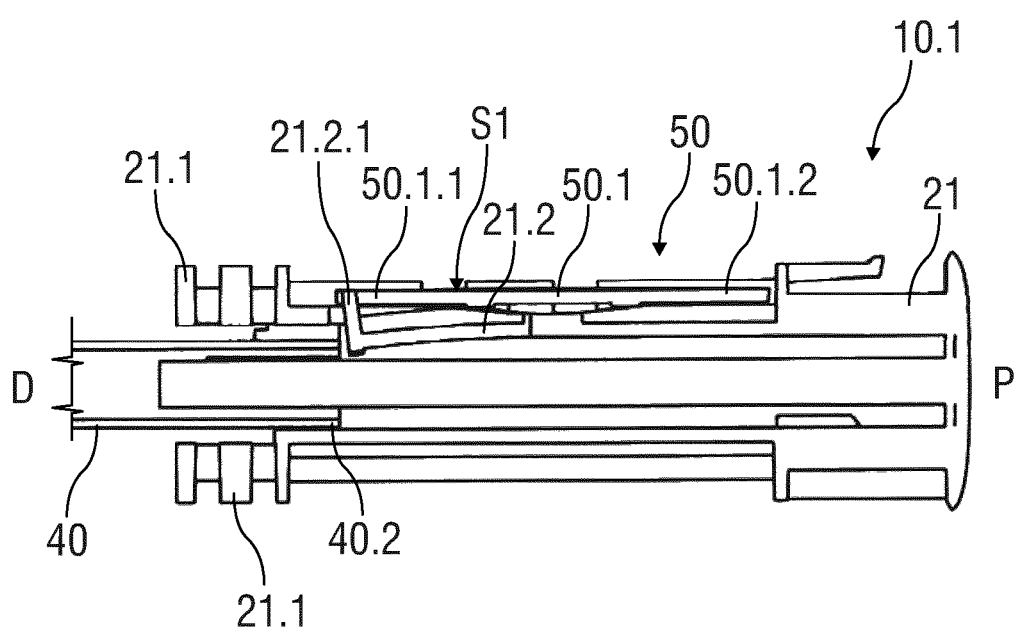
FIG. 10 is a longitudinal section of the drive sub assembly with the audible and/or tactile indicator according to FIG. 9 in a relaxed state.

FIGS. 9 and 10 are longitudinal sections of a drive subassembly 10.1 of the drug delivery device 10 and the audible and/or tactile indicator 50 in an assembled state. FIG. 9 illustrates the audible and/or tactile indicator 50 in the biased state S2. FIG. 10 illustrates the audible and/or tactile indicator 50 in the relaxed state S2.

The drive sub assembly 10.1 is a sub assembly of the drug delivery device 10 and comprises the components required to deliver the drug. The drive subassembly 10.1 comprises the proximal region 21 of the housing 11, the plunger 40 and the audible and/or tactile indicator 50. The drug delivery device 10 further comprises a front sub assembly (not shown separately) to allow for flexibility as to the time and location of manufacture of the subassemblies and final assembly with the syringe 24.

The illustrated proximal region 21 of the housing 11 comprises two support arms 21.1 adapted to support an axial position of the syringe 24 during storage, transportation and medicament delivery. The support arms 21.1 project distally from a distal end of the proximal region 21 of the housing 11. The proximal region 21 of the housing 11 further comprises an additional flexible arm 21.2 that projects distally from the distal end of the proximal region 21 of the housing 11 as well. The flexible arm 21.2 is adapted to damp impact forces and thus to stabilize the resilient force member 50.1 in its biased state S2 during storage, transportation, and medicament delivery.

The resilient force member 50.1 is in the biased state S2 and held in the proximal region 21 of the housing 11 by the snap connection as described above. The distal end face 50.1.1 of the resilient force member 50.1 is supported by a projection 21.2.1 of the flexible arm 21.2 arranged on a distal end of the flexible arm 21.2. The proximal end face 50.1.2 of the resilient force member 50.1 is free and not in contact with any other component and located above the flexible arm 21.2 or another section of the proximal region 21 of the housing 11. In an exemplary embodiment, the proximal region 21 of the housing 11 may comprise a plurality of flexible arms 21.2 that are arranged around a circumference of the proximal end of the proximal region 21 of the housing 11. Furthermore, the flexible arm 21.2 is deflected outwards supported by the outer circumference of the plunger 40.

After transition of the audible and/or tactile indicator 50 from the relaxed state S1 into the biased state S2 as described before, only a small force is required to hold the resilient force member 50.1 in the biased state S2. This is achieved by the longitudinal round fold 50.2 that provides a bent cross section of the resilient force member 50.1 which buckles into a new configuration by changing from the relaxed state S1 into the biased state S2. In this configuration, a stiffness of the material structure is significantly reduced and thus only a small holding force is required to maintain the resilient force member 50.1 in the biased state S2.

At the end of a drug delivery process, the resilient force member 50.1 is in the relaxed state S1 as illustrated in FIG. 10.

For delivering the drug through the needle 17 into an injection site, e.g. a patient's skin, the plunger 40 is moved distally from a proximal position to a distal position due to an activation of the drive spring 30 (not illustrated). The activation of the drive spring 30 may be initiated by pressing a button or by depressing the needle sleeve 13 as it is pushed against the injection site.

In the present FIG. 10, the plunger 40 has reached the distal position, wherein the flexible arm 21.2 is no longer engaged with the plunger 40. When the proximal plunger section 40.1, comprising the increased diameter with respect to the distal plunger section 40.2, passes the distal end of the flexible arm 21.2, the flexible arm 21.2 is allowed to relax and can thus move radially inwards driven by the distal end face 50.1.1. As the distal end face 50.1.1 moves, the resilient force member 50.1 can transition from a generally biased state S2 into a generally relaxed state S1 releasing stored energy to generate an audible signal, such as a click noise, due to a transition from the second conformation to the first conformation. Due to the large amount of stored energy, the audible signal can be generated with a high intensity, e. g. up to 100 decibels Signals of lesser intensity can also be generated. The proximal end face 50.1.2 can also swing radially inwards, thereby hitting the flexible arm 21.2 or the housing 11 or another component of the drug delivery device 10. This impact may also contribute to the generation of the audible signal.

The user or patient recognizing the audible signal knows that the drug delivery process is finished and that the full dose was spent.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 drive sub assembly
11 housing
11a window
12 cap assembly
13 needle sleeve
17 needle
20 distal region of the housing
21 proximal region of the housing
21.1 support arm
21.2 flexible arm
21.2.1 projection
22 button
23 piston
24 syringe
30 energy source, e.g. drive spring
40 plunger
40.1 proximal plunger section
40.2 distal plunger section
50 audible and/or tactile indicator
50.1 resilient force member
50.1.1 distal end face
50.1.2 proximal end face
50.2 longitudinal round fold
50.3 support tab
50.3.1 free end
50.4 notch
L longitudinal axis of the resilient force member
A cross axis of the resilient force member
X longitudinal axis of the drug delivery device
Y cross axis of the drug delivery device

The invention claimed is:

1. An audible and/or tactile indicator for use with a drug delivery device, the audible and/or tactile indicator comprising a resilient force member configured to reside in two or more states having two or more different conformations,
  wherein in a relaxed state of the two or more states, the resilient force member is relaxed in a first conformation,
  wherein in a biased state of the two or more states, the resilient force member is biased to store energy in a second conformation different from the first conformation,
  wherein the resilient force member is configured to release stored energy to generate an audible signal when changing from the biased state into the relaxed state due to a transition from the second conformation to the first conformation,
  wherein the resilient force member is bent by a certain angle about a longitudinal axis forming a longitudinal round fold with two adjacent angled wing-shaped sections, and
  wherein a notch is formed in the longitudinal round fold.

2. The audible and/or tactile indicator of claim 1, wherein the notch extends transversely to the longitudinal round fold.

3. The audible and/or tactile indicator of claim 1, wherein the longitudinal round fold has a bend radius between 1.5 mm and 2 mm.

4. The audible and/or tactile indicator of claim 1, wherein the notch is centrically arranged in the longitudinal round fold with respect to the longitudinal axis.

5. The audible and/or tactile indicator of claim 1, wherein a supporting tab is arranged on a region of at least one of the two adjacent angled wing-shaped sections extending between the notch and one of two end faces of the resilient force member.

6. The audible and/or tactile indicator of claim 1, wherein the resilient force member is configured as a leaf spring having a rectangular shape, a square shape, or an oval shape.

7. The audible and/or tactile indicator of claim 1, wherein the resilient force member is bent about the longitudinal round fold such that the two adjacent angled wing-shaped sections are at an angle of between 130 degrees and 160 degrees relative to each other.

8. The audible and/or tactile indicator of claim 1, wherein the resilient force member is configured as a bistable spring element.

9. The audible and/or tactile indicator of claim 1, wherein the resilient force member is supported in the biased state in order to prevent transition into the relaxed state.

10. The audible and/or tactile indicator of claim 1, wherein resilient force member is configured to be changed from the biased state to the relaxed state by a movement of a plunger that is used to displace a drug from a medicament container.

11. The audible and/or tactile indicator of claim 1, wherein at least one of the two adjacent wing-shaped sections comprises a supporting tab outwardly protruding from a long side of the at least one of the two adjacent wing-shaped sections.

12. The audible and/or tactile indicator of claim 11, wherein the supporting tab has a free end which is outwardly bent.

13. A drug delivery device comprising a resilient force member of an audible and/or tactile indicator, the resilient force member configured to reside in two or more states having two or more different conformations,
wherein in a relaxed state of the two or more states, the resilient force member is relaxed in a first conformation,
wherein in a biased state of the two or more states, the resilient force member is biased to store energy in a second conformation different to the first conformation,
wherein the resilient force member is configured to release stored energy to generate an audible signal when changing from the biased state into the relaxed state due to a transition from the second conformation to the first conformation,
wherein the resilient force member is bent by a certain angle about a longitudinal axis forming a longitudinal round fold with two adjacent angled wing-shaped sections, and
wherein a notch is formed in the longitudinal round fold.

14. The drug delivery device of claim 13, wherein the resilient force member is configured to be changed from the biased state to the relaxed state by a movement of a plunger towards a distal position at the end of a drug delivery process.

15. The drug delivery device of claim 13, wherein the resilient force member is configured to transition from the biased state into the relaxed state when a proximal plunger section abuts a distal end face of the resilient force member.

16. The drug delivery device of claim 13, wherein the resilient force member is supported when the drug delivery device is in an initial state and the resilient force member is unsupported when the drug delivery device is in a primed state.

17. The drug delivery device of claim 13, wherein the resilient force member is supported when the drug delivery device is in an initial state and in a primed state and a distal end face of the resilient force member is supported by a supporting protrusion arranged on a proximal region of a housing.

18. The drug delivery device of claim 13, wherein the resilient force member is unsupported in the biased state.

19. The drug delivery device of claim 13, wherein the resilient force member is radially unsupported in the biased state.

20. The drug delivery device of claim 13, wherein in the biased state, the resilient force member is deformed to store energy.

21. An audible and/or tactile indicator for use with a drug delivery device, the audible and/or tactile indicator comprising a resilient force member configured to reside in two or more states having two or more different conformations,
wherein in a relaxed state of the two or more states, the resilient force member is relaxed in a first conformation,
wherein in a biased state of the two or more states, the resilient force member is biased to store energy in a second conformation different from the first conformation,
wherein the resilient force member is configured to release stored energy to generate an audible signal when changing from the biased state into the relaxed state due to a transition from the second conformation to the first conformation,
wherein the resilient force member is bent by a certain angle about a longitudinal axis forming a longitudinal round fold with two adjacent angled wing-shaped sections, and
wherein at least one of the two adjacent wing-shaped sections comprises a supporting tab having a first portion and a second portion, wherein the first portion is bent relative to the second portion.

22. The audible and/or tactile indicator of claim 21, wherein the supporting tab outwardly protrudes from a side of the at least one of the two adjacent wing-shaped sections.

23. The audible and/or tactile indicator of claim 21, wherein the first portion of the supporting tab is bent relative to the second portion of the supporting tab about an axis parallel to the longitudinal axis.

24. The audible and/or tactile indicator of claim 21, wherein the first portion of the supporting tab is bent relative to the second portion of the supporting tab about an axis angled relative to the longitudinal axis.

25. The audible and/or tactile indicator of claim 21, wherein the first portion of the supporting tab is bent relative to the second portion in an opposite direction as the longitudinal round fold such that a free end of the supporting tab is bent upward.

26. The audible and/or tactile indicator of claim 21, wherein the first portion of the supporting tab is bent relative to the second portion in a same direction as the longitudinal round fold such that a free end of the supporting tab is bent downward.

* * * * *